(12) United States Patent
Miller et al.

(10) Patent No.: US 8,269,828 B2
(45) Date of Patent: Sep. 18, 2012

(54) THERMAL DISSIPATION FOR IMAGER HEAD ASSEMBLY OF REMOTE INSPECTION DEVICE

(75) Inventors: Jeffrey J. Miller, Northville, MI (US); Al Boehnlein, Ypsilanti, MI (US); Tye Newman, Howell, MI (US)

(73) Assignee: Perceptron, Inc., Plymouth, MI (US)

( * ) Notice: Subject to any disclaimer, the term of this patent is extended or adjusted under 35 U.S.C. 154(b) by 1065 days.

(21) Appl. No.: 12/038,337

(22) Filed: Feb. 27, 2008

(65) Prior Publication Data

US 2008/0158349 A1 Jul. 3, 2008

Related U.S. Application Data

(63) Continuation-in-part of application No. 11/645,280, filed on Dec. 22, 2006, now abandoned.

(51) Int. Cl.
*H04N 3/36* (2006.01)
(52) U.S. Cl. .................................................. 348/80
(58) Field of Classification Search .............. 348/80
See application file for complete search history.

(56) References Cited

U.S. PATENT DOCUMENTS

| 6,229,563 | B1 | 5/2001 | Miller, II et al. |
| 6,551,240 | B2 * | 4/2003 | Henzler ..................... 600/179 |
| 6,796,939 | B1 * | 9/2004 | Hirata et al. ............... 600/179 |
| 6,831,679 | B1 * | 12/2004 | Olsson et al. ............... 348/84 |
| 7,311,453 | B2 | 12/2007 | Li |
| 7,335,159 | B2 * | 2/2008 | Banik et al. ............... 600/156 |
| 7,413,543 | B2 * | 8/2008 | Banik et al. ............... 600/129 |
| 2004/0199052 | A1 * | 10/2004 | Banik et al. ............... 600/142 |
| 2006/0004258 | A1 * | 1/2006 | Sun et al. .................. 600/160 |
| 2006/0171693 | A1 * | 8/2006 | Todd et al. ................. 396/17 |
| 2007/0173695 | A1 * | 7/2007 | Hirata ....................... 600/152 |
| 2007/0195521 | A1 * | 8/2007 | Rosiello .................... 362/202 |

FOREIGN PATENT DOCUMENTS

KR 2002-0004721 1/2002

* cited by examiner

*Primary Examiner* — Tammy Nguyen
(74) *Attorney, Agent, or Firm* — Harness, Dickey & Pierce, P.L.C.

(57) ABSTRACT

An imager head assembly for a remote inspection device includes an imager housing. A circuit board is positioned within the imager housing. The circuit board has a light emitting diode connected thereto. A thermally conductive material in contact with the circuit board and the imager housing creates a conductive heat transfer path to dissipate heat generated by the light emitting diode through the imager housing. A light transmissive light pipe unit can be positioned proximate the circuit board to permit light emitted by the light emitting diode to pass through the light pipe unit.

13 Claims, 11 Drawing Sheets

THERMAL DISSIPATION FOR IMAGER HEAD ASSEMBLY OF REMOTE INSPECTION DEVICE

CROSS-REFERENCE TO RELATED APPLICATIONS

This application is a continuation-in-part of U.S. patent application Ser. No. 11/645,280 filed on Dec. 22, 2006. The disclosure of the above application is incorporated herein by reference.

FIELD

The present disclosure relates to imager head assemblies for borescopes and video scopes and methods for dissipating heat from the imager head assemblies.

BACKGROUND

The statements in this section merely provide background information related to the present disclosure and may not constitute prior art.

Borescopes and video scopes used for inspecting visually obscure locations, hereinafter referred to as remote inspection devices, are typically tailored for particular applications. For instance, some remote inspection devices have been tailored for use by plumbers to inspect pipes and drains. Likewise, other types of remote inspection devices have been tailored for use by mechanics to inspect interior compartments of machinery being repaired.

Analog remote inspection devices are known which have hand-held control units using a power source such as a plurality of batteries, with data leads and power lines extending through a flexible cable to an image receiving head. Such devices commonly provide a remote light source to illuminate the area of interest and an imaging device to capture the illuminated image. Images provided by analog signal devices are adequate for many applications, however, where fine image detail is desired analog signal devices cannot convey enough data to improve the resolution. An increased power light source can also be used, however, increasing light source power detrimentally locally increases the heat generated which complicates the imaging device configuration.

SUMMARY

According to several embodiments of the present disclosure, an imager head assembly for a remote inspection device includes an imager housing. A circuit board is positioned within the imager housing. A light emitting diode is connected to the circuit board. A thermally conductive material in contact with both the circuit board and the imager housing creates a conductive heat transfer path to dissipate heat generated by the light emitting diode through the imager housing.

According to other embodiments an imager head assembly for a remote inspection device includes an imager housing. A circuit board is positioned within the imager housing. The circuit board has a light emitting diode connected thereto. A light transmissive light pipe unit is positioned proximate the circuit board to permit light emitted by the light emitting diode to pass through the light pipe unit. A thermally conductive material in contact with the circuit board and the imager housing creates a conductive heat transfer path to dissipate heat generated by the light emitting diode through the imager housing.

According to still further embodiments, an imager head assembly for a remote inspection device includes an imager nut adapted to connect to an imager body. A first circuit board is positioned between the imager body and the imager nut. The first circuit board has four equidistantly spaced high power light emitting diodes connected thereto operating to generate light to illuminate an object located proximate to the imager head assembly. A second circuit board is positioned within the imager body having an imager device connected to the second circuit board. The imager device is adapted to receive the light emitted by the light emitting diodes and reflected off the object and transmit a digital signal representing an image of the object. A thermally conductive material in contact with both the first circuit board and the imager body creates a conductive heat transfer path to dissipate heat generated by the light emitting diodes through the imager body.

In still other embodiments, a remote inspection device includes a display housing having an image view screen. A flexible tube extends from the display housing. An imager housing is connected to the flexible tube and electrically connected to the display housing. A circuit board is positioned within the imager housing. A light emitting diode is connected to the circuit board. A thermally conductive material in contact with the circuit board and the imager housing creates a conductive heat transfer path to dissipate heat generated by the light emitting diode through the imager housing.

In other embodiments, a method for configuring an imager head assembly for a remote inspection device includes positioning a thermally conductive material in contact with the circuit board and the imager housing to create a conductive heat transfer path to dissipate heat generated by the light emitting diode through the imager housing.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
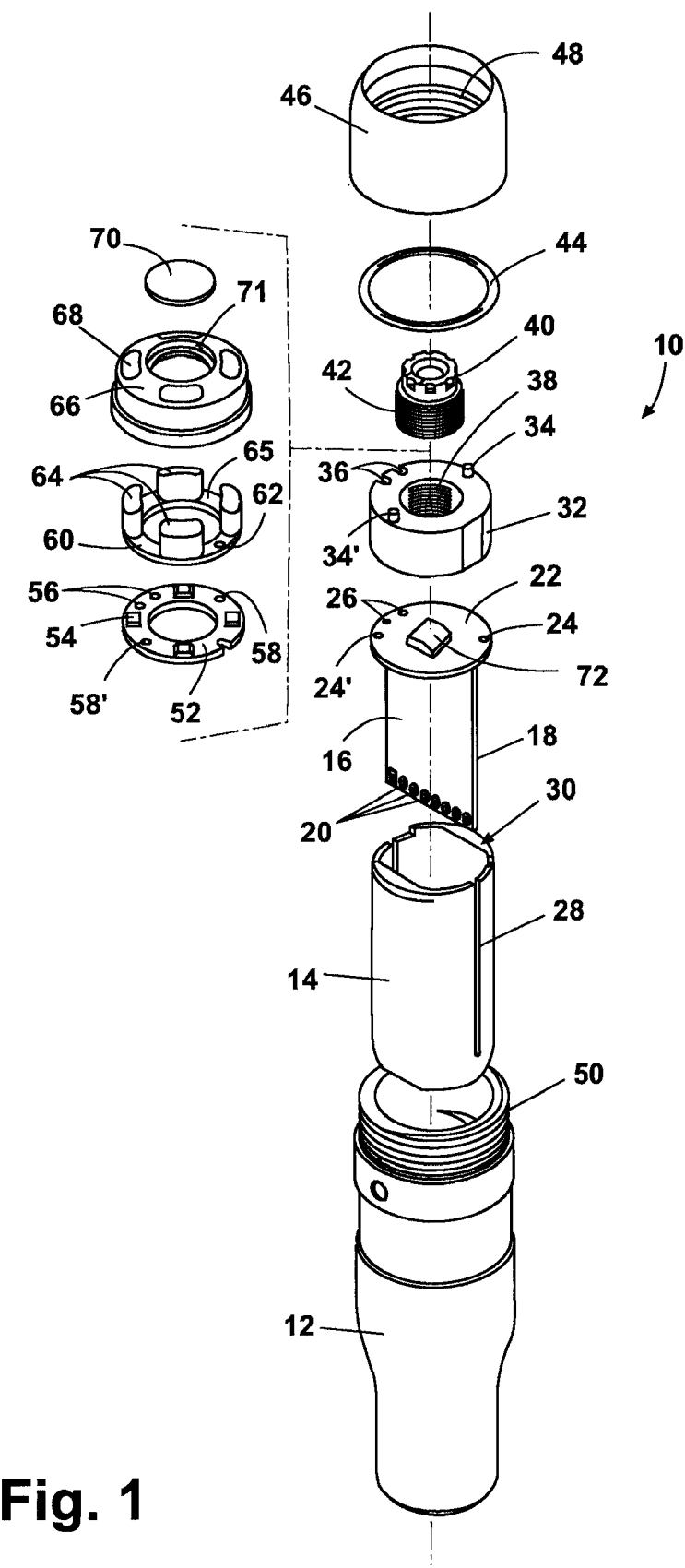
FIG. 1 is an assembly view of the component parts of an imager head assembly of the present disclosure.

The following description is merely exemplary in nature and is not intended to limit the present disclosure, application, or uses. It should be understood that throughout the drawings, corresponding reference numerals indicate like or corresponding parts and features.

Referring to FIG. 1, an imager head assembly 10 includes an imager body 12 which slidably receives an imager PCB (printed circuit board) mount/isolator 14 which in turn is adapted to receive a circuit board assembly 16. Circuit board assembly 16 includes a first circuit board 18 having a plurality of wiring receiving and connection apertures 20 and a second circuit board 22. Second circuit board 22 provides alignment pin apertures 24, 24' and a plurality of wiring through apertures 26. Circuit board assembly 16 is adapted to be slidably received in a tapered slot 28 of imager PCB mount/isolator 14. Circuit board assembly 16 is slidably inserted into imager PCB mount/isolator 14 until second circuit board 22 contacts a flange end 30 of imager PCB mount/isolator 14.

Imager head assembly 10 further includes a lens mount 32 which includes a plurality of alignment pins 34, 34' and a plurality of wiring slots 36 which are coaxially alignable with the wiring through apertures 26 of second circuit board 22. A plurality of internal threads 38 are also provided in lens mount 32. According to several embodiments, lens mount 32 can be a polymeric material which is molded into the shape shown or can also be a metal material which is shaped or machined to provide the details shown. Lens mount 32 can also have a plurality of alignment pins (shown in FIG. 9) which are created on a bottom side of lens mount 32 and aligned to be slidably received in alignment pin apertures 24, 24' of second circuit board 22.

An imaging lens 40 having a plurality of external male threads 42 is adapted to be threadable received by the plurality of internal threads 38 of lens mount 32. Imaging lens 40 is axially adjustable using external male threads 42 to control a focal length of the imager head assembly 10. Imaging lens 40 can also be remotely focused.

A seal member 44 such as an O-ring is positionable within an internal diameter of an imager nut 46 such that the seal member 44 provides a moisture and air seal between imager nut 46 and imager body 12. A plurality of internal threads 48 are provided with imager nut 46 so that imager nut 46 can be threadably engaged with imager body 12. According to several embodiments, both imager nut 46 and imager body 12 are created from a metal material such as aluminum. The imager body 12 and the imager nut 46 when connected together as shown in reference to FIG. 3 define an imager housing.

Light is emitted by the imager head assembly 10 by energizing a plurality of LEDs (light emitting diodes) 54 which are fixed to a printed circuit board or LED board 52. In the exemplary embodiment shown, four LEDs 54 are equidistantly spaced from each other about a perimeter of a substantially circular-shaped LED board 52. The LEDs 54 are equidistantly spaced from each other to transmit the light evenly and to dissipate the heat generated by the LEDs 54 evenly about LED board 52. LEDs 54 operate to generate light to illuminate a local object (not shown) within a predetermined focal range of the imager head assembly 10. LED board 52 also provides a plurality of wiring through apertures 56 which are coaxially alignable with wiring slots 36 of lens mount 32 and with wiring through apertures 26 of second circuit board 22. Wiring through apertures 56, wiring slots 36, and wiring through apertures 26 are provided to allow for passage of electrical power leads for connection with LEDs 54 of LED board 52. A plurality of alignment pin apertures 58 are also provided in LED board 52 which slidably receive the alignment pins 34, 34' of lens mount 32 so that LED board 52 is non-rotatably mounted to lens mount 32.

A light pipe unit 60 is positioned above (as viewed in FIG. 1) LED board 52 such that a plurality of alignment pin apertures 62 coaxially align with alignment pin apertures 58, 58' to also receive a portion of each of the alignment pins 34, 34' extending from lens mount 32. Light pipe unit 60 is therefore non-rotatably engaged to LED board 52 such that a plurality of light pipes 64 is coaxially positioned with respect to each of the LEDs 54. Light pipe unit 60 can be constructed by molding a transparent polymeric material to form both a base ring 65 and the light pipes 64 which transversely extend from the base ring 65.

An imager cap 66 is positioned above (as viewed in FIG. 1) and slidably inserted over the light pipe unit 60 such that a plurality of light passages 68 created in imager cap 66 are coaxially aligned with and slidably receive each of the individual light pipes 64 of light pipe unit 60. The light emitted by each of the LEDs 54 is transmitted through the light pipes 64 and the light passages 68 to illuminate an area adjacent to imager head assembly 10.

A light receiving window 70 which according to several embodiments is created from a sapphire material can be substantially round in shape and adapted to fit within a receiving space 71 such as a counter-bore created in imager cap 66. Light receiving window 70 can also be provided of other materials with design criteria being a resistance to scratching or marring from the local environment within which imager head assembly 10 will function, as well as the capability of transmitting substantially 100% of the light that is reflected into light receiving window 70. The reflected light which is received through light receiving window 70 is received by an imager device 72 which is fixed to second circuit board 22. Imager device 72 converts the image received to a digital signal for remote transmission and readout.

Figure 2:
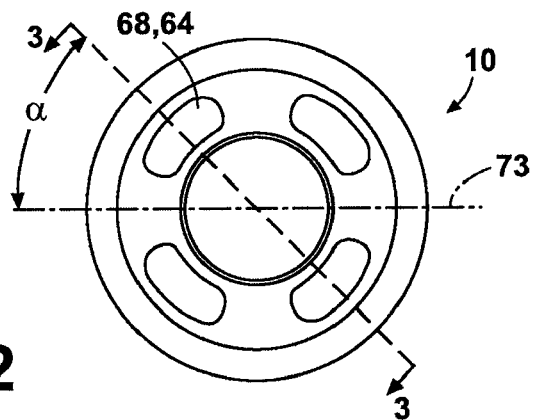
FIG. 2 is a top plan view of the imager head assembly of FIG. 1 shown in an assembled condition.

Referring to FIG. 2, as previously noted each of the light passages 68 and coaxially aligned light pipes 64 are equidistantly spaced from each other and in the exemplary embodiment shown have four (4) each of the light passages 68 and light pipes 64. The light passages 68 and light pipes 64 are oriented at an angle $\alpha$ with respect to an alignment axis 73. According to several embodiments, angle $\alpha$ is approximately 45°, but can vary as the quantity of light passages 68 and light pipes 64 vary.

Figure 3:
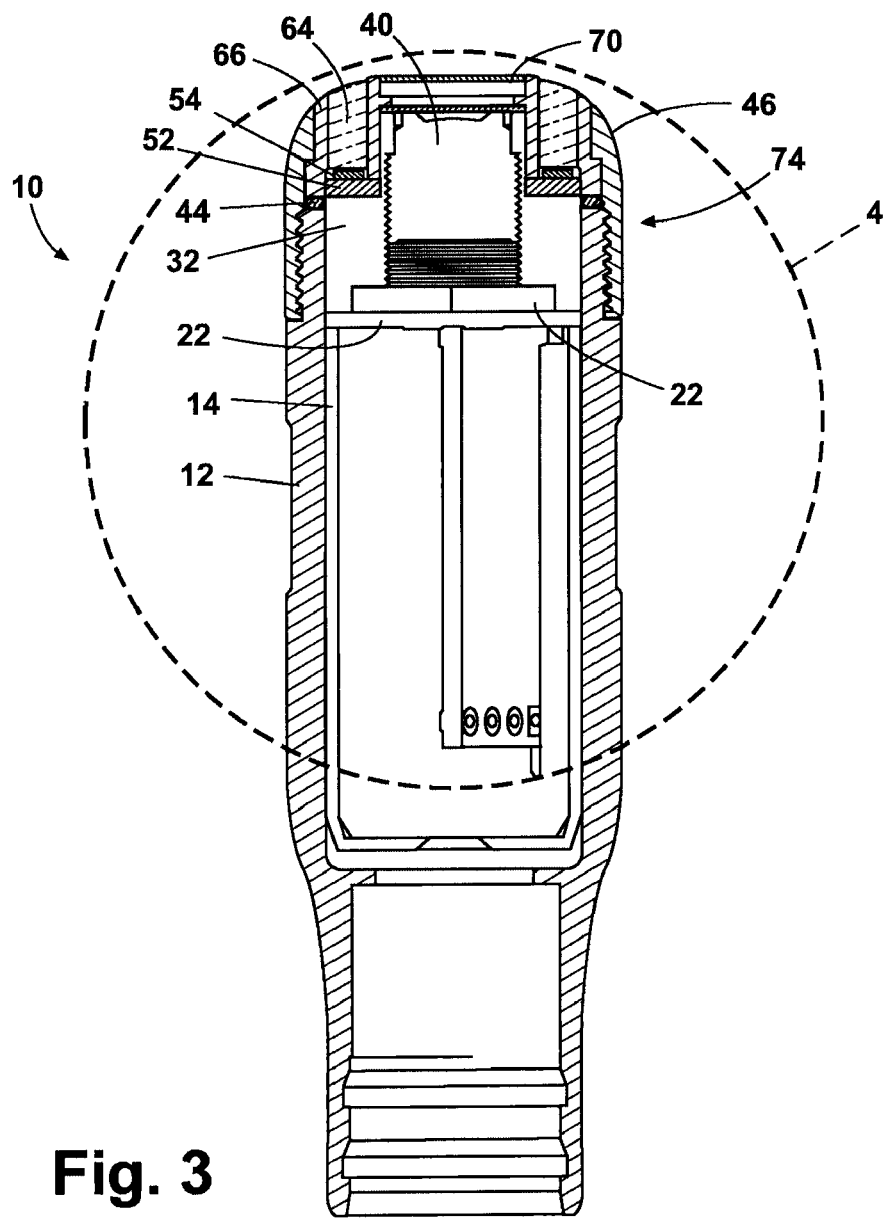
FIG. 3 is a partial cross sectional front elevational view taken at section 3 of FIG. 1.

Referring to FIG. 3, an imager head sub-assembly 74 according to several embodiments includes a configuration having imager nut 46 threadably engaged with imager body 12. Imaging lens 40 is threadably received within lens mount 32 which also forms a support surface for LED board 52. LED board 52 in turn provides support for imager cap 66 and light pipe unit 60 including each of the individual ones of the light pipes 64. As shown, each of the LEDs 54 are aligned for light transmission through the individual ones of the light pipes 64.

Light transmitted by LEDs 54 and reflected by an object (not shown) and received through light receiving window 70 is transmissible through imaging lens 40 to reach second circuit board 22.

Figure 4:
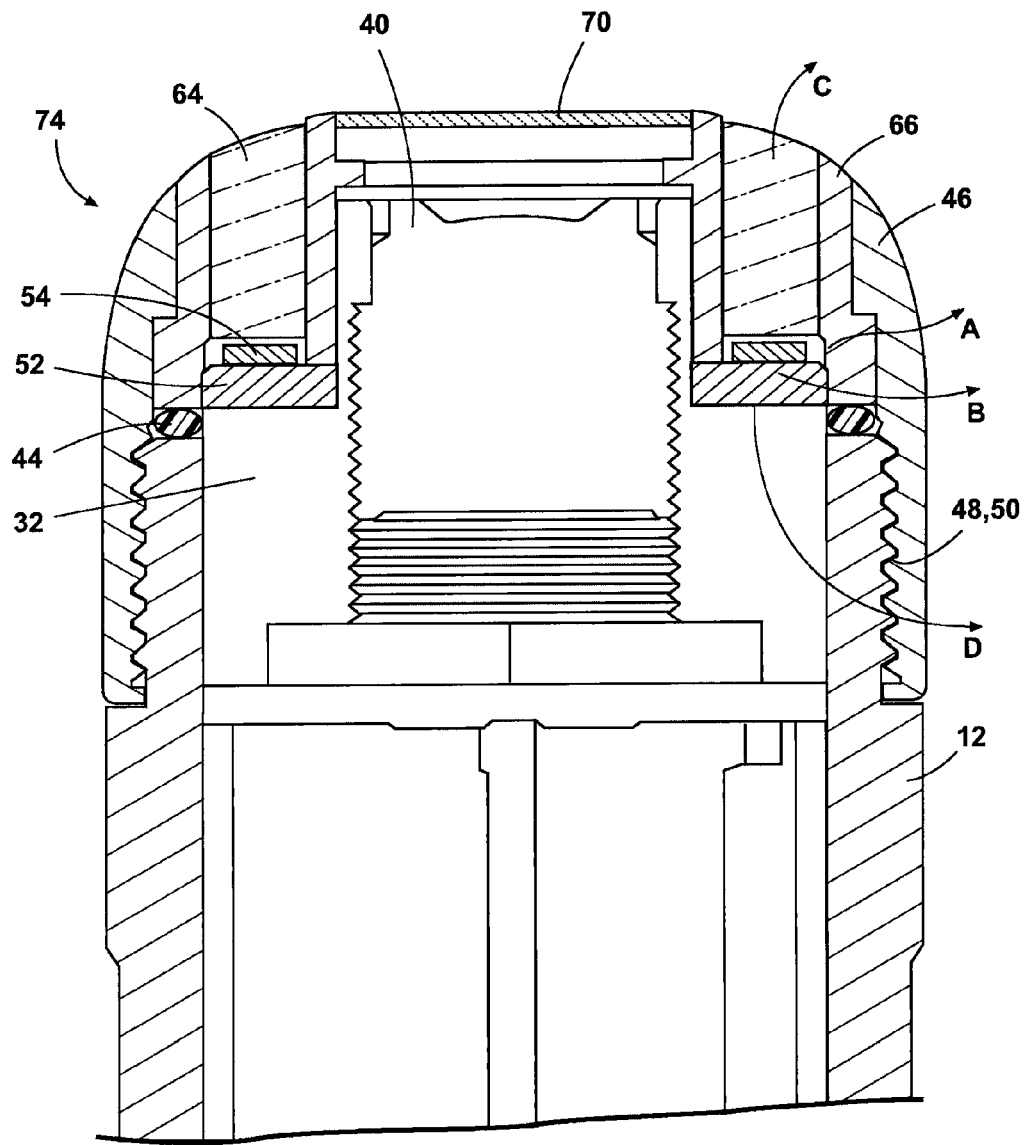
FIG. 4 is a partial cross sectional front elevational view taken at area 4 of FIG. 1.

Referring to FIG. 4, heat generated by each of the LEDs 54 must be efficiently removed from LED board 52 to prevent potential damage to the LEDs 54 and/or the LED board 52. Several heat transmission paths are shown in FIG. 4 which are each maximized by the selective use of materials having a high coefficient of thermal transfer. A first heat transmission path "A" conductively dissipates heat generated by the LEDs 54 by contact between a metal material such as aluminum of imager cap 66 and the metal material of imager nut 46. A second heat transmission path "B" is also provided by physical contact between LED board 52, the imager cap 66, and the imager nut 46 which also provides a convective heat transfer path. A third heat transmission path "C" is provided through each of the light pipes 64. Due to an air gap above the LEDs 54, the third heat transmission path "C" initially requires radiant heat transfer between LEDs 54 and each of the light pipes 64. It is therefore desirable to maximize the amount of heat transmission away from LEDs 54 by maximizing the physical contact and therefore conductive heat transfer between the various materials of LED board 52, imager cap 66, and imager nut 46.

Figure 5:
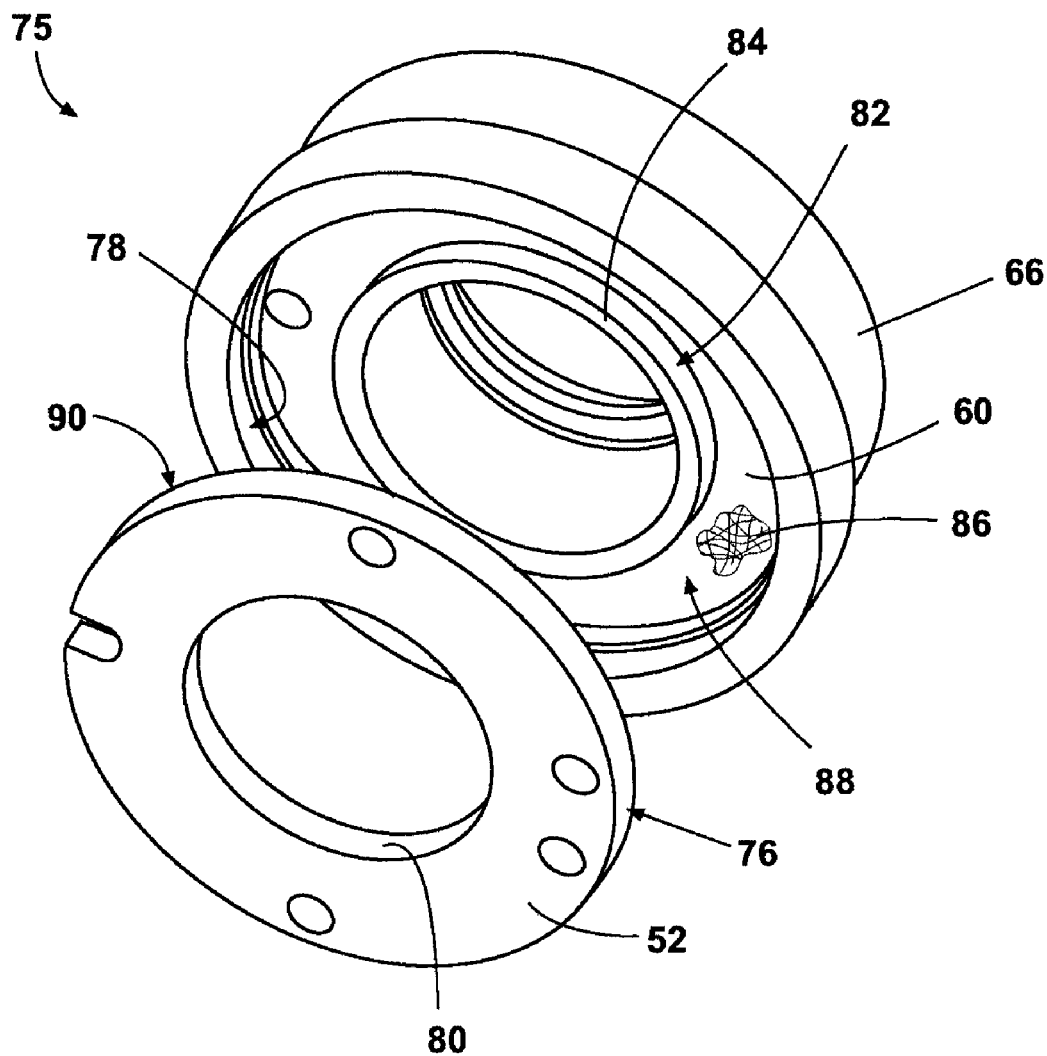
FIG. 5 is a rear perspective view of a sub-assembly of the imager cap, light pipe, and LED board prior to engagement of the LED board.

Referring to FIG. 5, according to several embodiments one of the preferred methods of maximizing heat transfer between LED board 52, light pipe unit 60, and imager nut 66 is provided by initially installing light pipe unit 60 by slidably inserting into imager cap 66. An outer perimeter surface 76 of LED board 52 is adapted to be slidably received within and maximize physical contact with an inner perimeter surface 78 of imager cap 66. Also, an inner bore surface 80 of LED board 52 is similarly adapted to be slidably received and to maximize physical contact with an outer sleeve surface 82 of a sleeve 84 of light pipe unit 60. Before connecting LED board 52 to the combination of light pipe unit 60 and imager cap 66, a light transmissive, thermally conductive adhesive 86 is applied over an entire face 88 of light pipe unit 60. A volume of light transmissive, thermally conductive adhesive 86 which is applied is sufficient so that an entire surface 90 of LED board 52 having LEDs 54 (not visible in this view) as well as outer perimeter surface 76, and inner bore surface 80 of LED board 52, is contacted by adhesive 86.

Adhesive 86 therefore provides both the holding force to retain LED board 52 as well as providing a light transmission path for each of the LEDs 54. By maximizing contact between both light pipe unit 60 and the imager cap 66, adhesive 86 also maximizes transmission of the heat generated by the LEDs 54 to both the light pipe unit 60 and the imager cap 66. According to several embodiments, adhesive 86 can be Part Number KER-2500AB provided by the Shin-Etsu Company, or as DOW-CORNING 732 adhesive. A thermal conductivity greater than that of air is desired for adhesive 86 such that the thermal conductivity "T"$\geq$0.025 W/(mK). By maximizing conductive heat transfer through imager cap 66 to the external portions of imager head assembly 10 including imager nut 46 and imager body 12, natural convective heat loss to ambient can thereafter take place.

Figure 6:
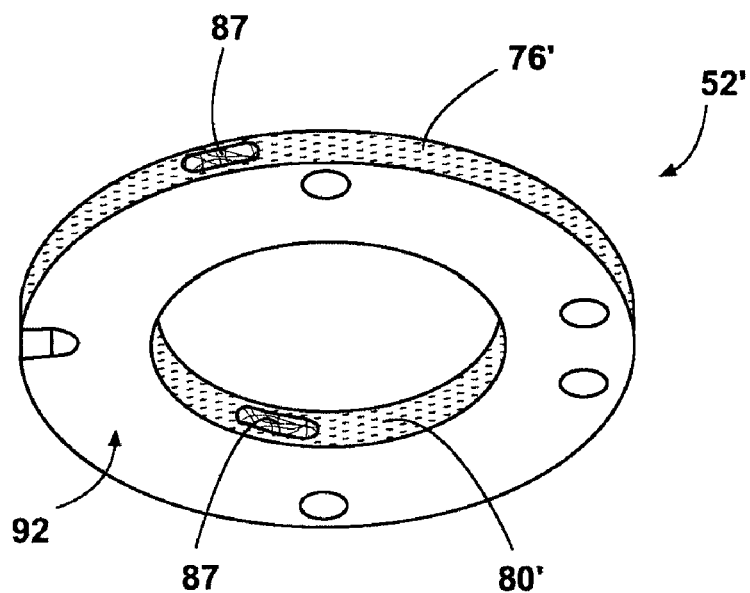
FIG. 6 is a rear elevational perspective view of another embodiment of an LED board.
Figure 7:
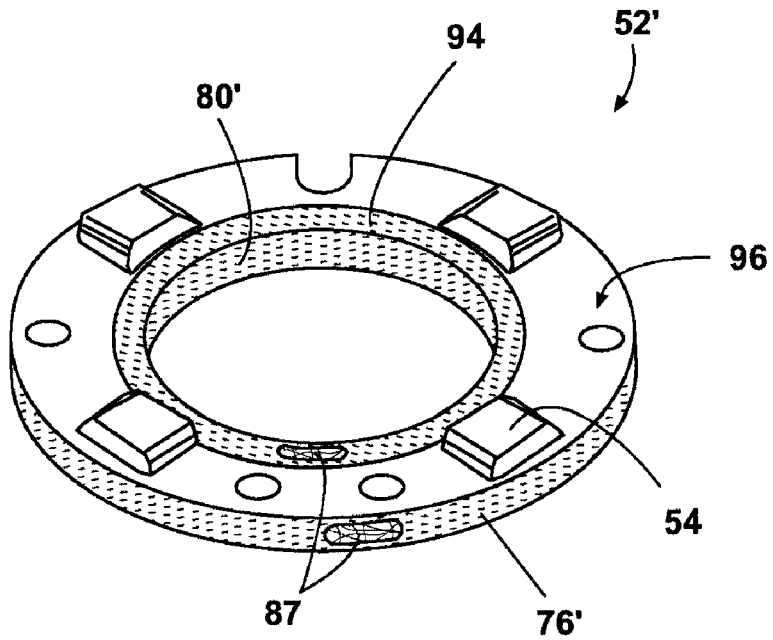
FIG. 7 is a front elevational perspective view of the LED board of FIG. 6.

Referring to FIGS. 6 and 7, according to additional embodiments of the present disclosure, a modified LED board 52' can be made from a thermally conductive circuit board material. The thermally conductive circuit board material is selected from a material having high thermal conductivity and low electrical conductivity at the surface of LED board 52'. The thermally conductive LED board 52' acts as a heat sink and transmission path for heat generated by the LEDs 54. LED board 52' conducts heat away from the LEDs 54 using a thermal interface material 87 covering specific areas of LED board 52' to maximize thermal conductivity to the exterior parts of imager head assembly 10. Thermal interface material 87 is placed on outer perimeter surface 76' and inner bore surface 80', but is not placed on an LED board rear surface 92. On the LED 54 side of LED board 52', thermal interface material 87 is placed on an inner diametrical LED mount face 94 which is inward of each of the LEDs 54, while an outer diametrical LED mount face 96 does not receive the thermal interface material 87.

Referring to FIG. 7 and again to FIG. 5, the thermal interface material 87 coated or placed on outer perimeter surface 76', inner bore surface 80', and inner diametrical LED mount face 94 maximizes heat transfer from LED board 52' to inner perimeter surface 78, and between outer sleeve surface 82 of imager cap 66 and light pipe unit 60, respectively.

Figure 8:
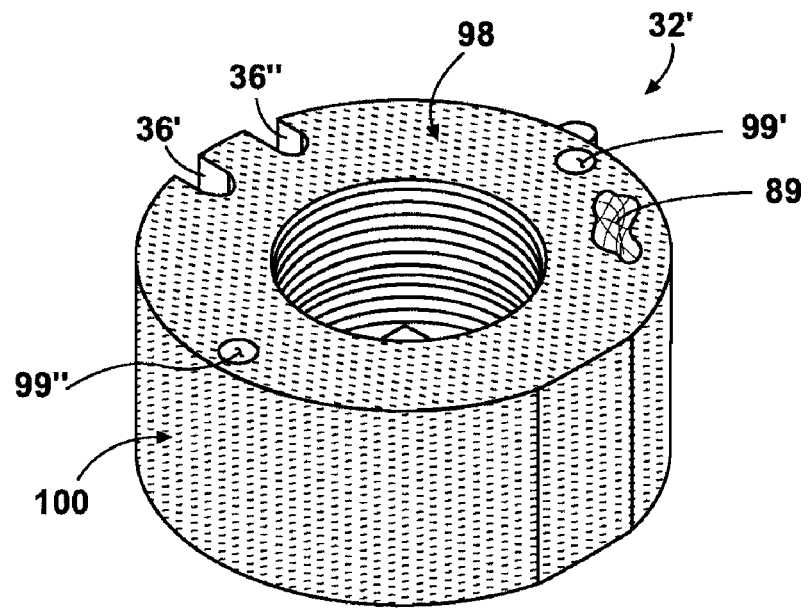
FIG. 8 is a front elevational view of a modified lens mount.
Figure 9:
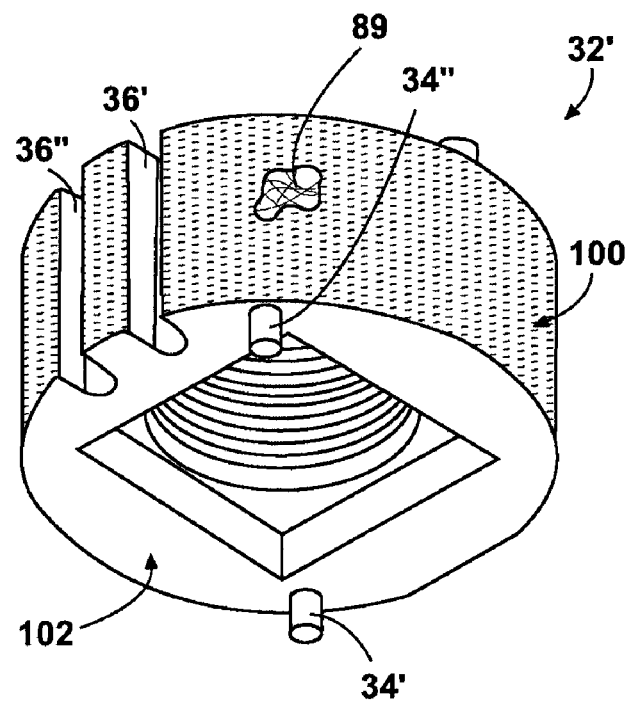
FIG. 9 is a bottom elevational view of the modified lens mount of FIG. 8.

Referring now to both FIGS. 8 and 9, according to additional embodiments, a lens mount 32' is modified from lens mount 32 to maximize transfer of heat generated by LED board 52 (not shown in this view) by constructing the lens mount 32' from a material possessing high thermal conductivity, very low electrical conductivity, and a low co-efficient of thermal expansion. Examples of material used for lens mount 32' include thermally conductive liquid crystal polymer (LCP), or thermally conductive polybutylene terephthalate (PBT). In addition to the selection of the specific material for lens mount 32', to further maximize heat transmission a thermal interface material (i.e., thermal grease) is deposited on the outer diameter of the lens mount 32' to further conduct heat from the lens mount 32' to the external parts of imager head assembly 10.

The shaded areas shown in FIGS. 8 and 9 of lens mount 32' represent locations where a thermally transmissive grease 89 can be applied to a first or upper LED board facing surface 98, with the exception of pin alignment apertures 99', 99" and wiring slots 36', 36". Further areas for application of thermal grease 89 include a perimeter surface 100. A second or lower lens mount surface 102 along with alignment pins 34', 34" do not receive thermal grease 89. Together with the increased heat transfer from use of the high thermal conductivity, very low electrical conductivity, and low co-efficient of thermal expansion material of lens mount 32', the addition of thermal grease 89 increases the contact or surface areas between lens mount 32', LED board 52, and imager body 12. As shown with further reference to FIG. 4, a fourth heat transmission path "D" is created by this embodiment.

Figure 10:
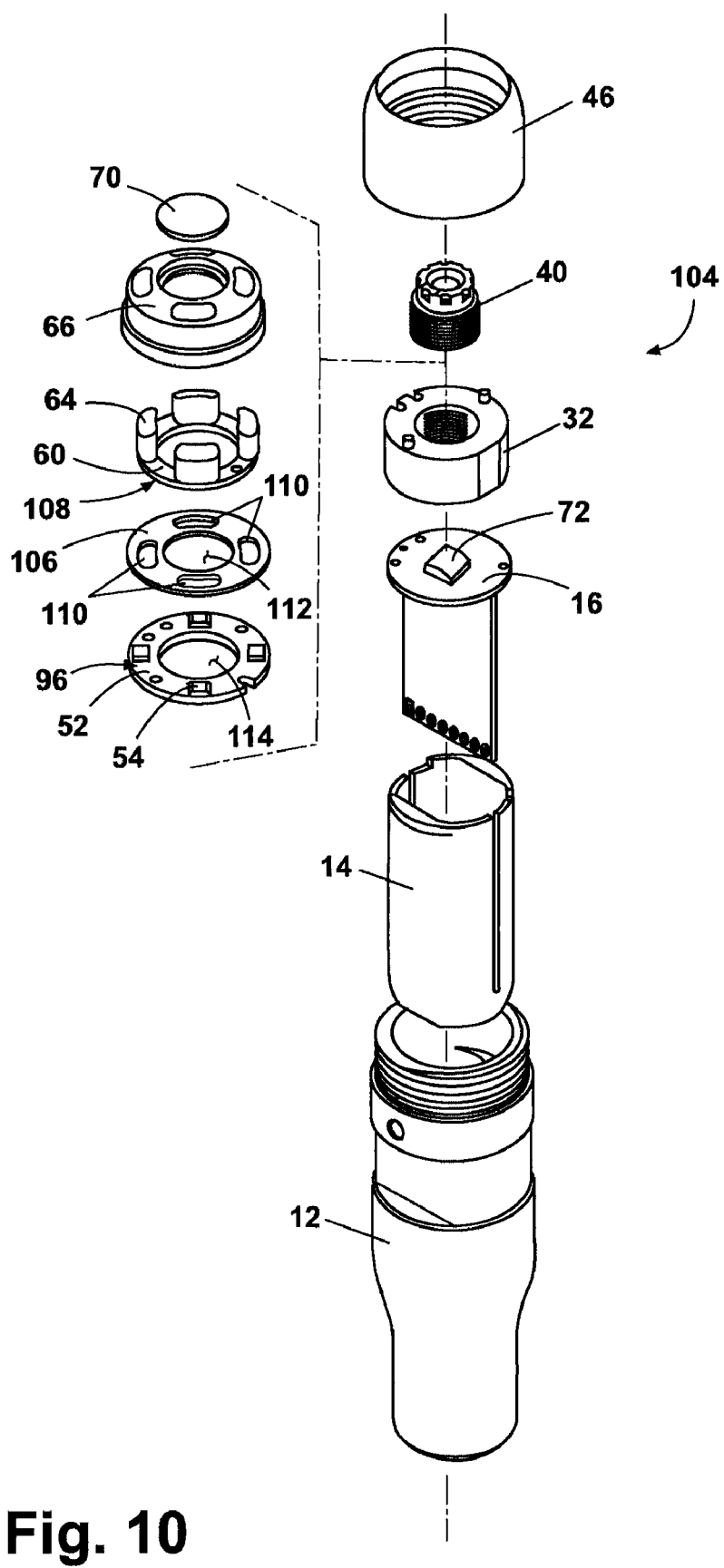
FIG. 10 is an assembly view of the component parts of another embodiment of an imager head assembly of the present disclosure.

Referring now to FIG. 10, according to still further embodiments, an imager head assembly 104 includes many of the components described in reference to imager head assembly 10, therefore the common component parts will not be further discussed. Imager head assembly 104 can be omitted from adhesive 86 and thermal interface material 87 and replaced by a thermal gasket 106 which contacts at least the outer diametrical LED mount face 96 of LED board 52 and further contacts a contact surface 108 of light pipe unit 60. A plurality of semi-circular elongated apertures 110 corresponding in location and size to each of the light pipes 64 are sized and oriented to provide clearance about each of the LEDs 54. A first imaging lens receiving aperture 112 is provided in thermal gasket 106 to allow light transmission received through light receiving window 70 to be received through a second imaging lens receiving aperture 114 of LED board 52, therefore permitting light transmitted through light receiving window 70 to reach imager device 72.

Thermal gasket 106 is preferably a thermally conductive gasket material. This material should also be flexible or compliant, having a gap filling property requiring resiliency, and can be cut from a sheet of thermally conductive, electrically insulating material such as Bergquist Company "GAP-PADVO", or St. Gobaain Co. "GAP-FILLER TC 3000" materials. The resiliency of thermal gasket 106 maximizes surface contact between LED board 52 and light pipe unit 60 to improve heat transmission through any of first, second, or third heat transmission paths "A", "B" or "C" shown in reference to FIG. 4.

Figure 11:
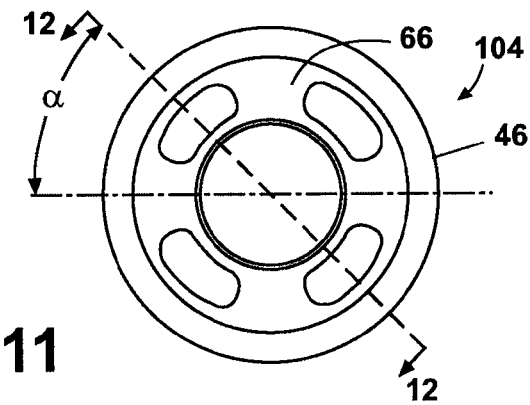
FIG. 11 is a top plan view of the imager head assembly of FIG. 10.
Figure 12:
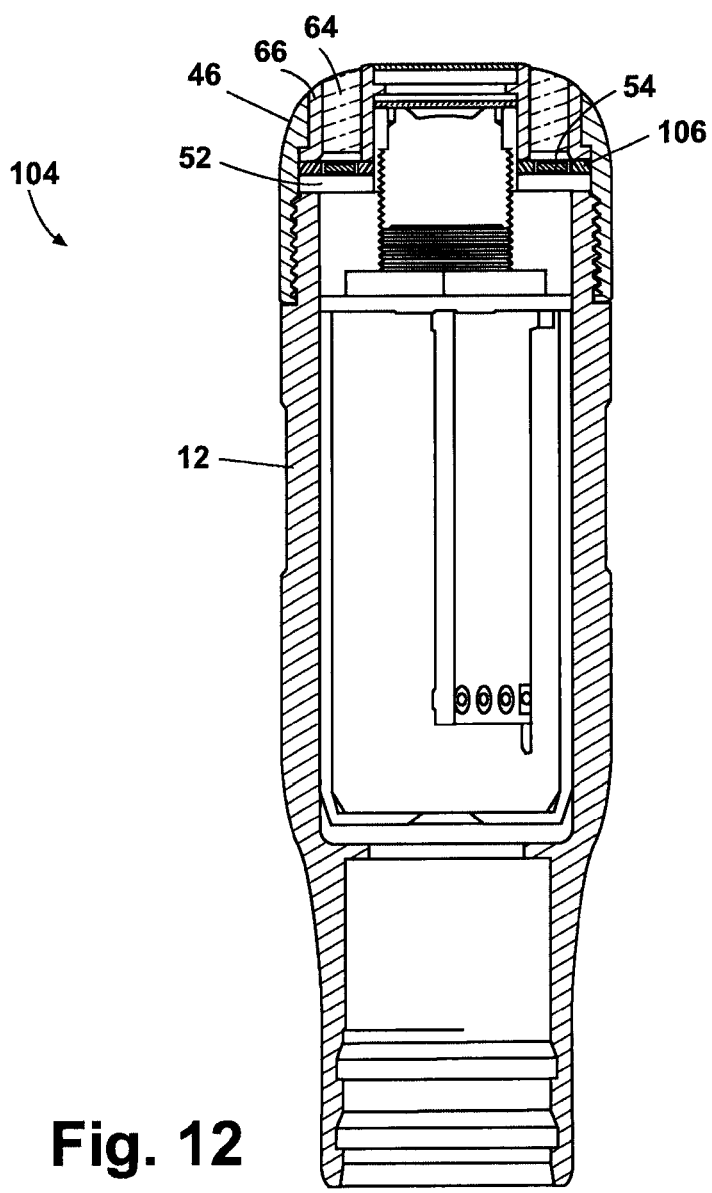
FIG. 12 is a partial cross sectional front elevational view taken at section 12 of FIG. 11.

Referring to FIGS. 11 and 12, imager head assembly 104 is outwardly similar in appearance to imager head assembly 10 such that imager nut 46 and imager cap 66 are oriented similar to imager head assembly 10 at window alignment angle α. With imager nut 46 threadably engaged with imager body 12, thermal gasket 106 is fixed and compressed between LED board 52 and each of the light pipes 64 and imager cap 66. Compression of thermal gasket 106 can also increase a diameter of thermal gasket 106 so thermal gasket 106 can physically contact imager nut 46 to further improve conductive heat transfer to imager nut 46.

Figure 13:
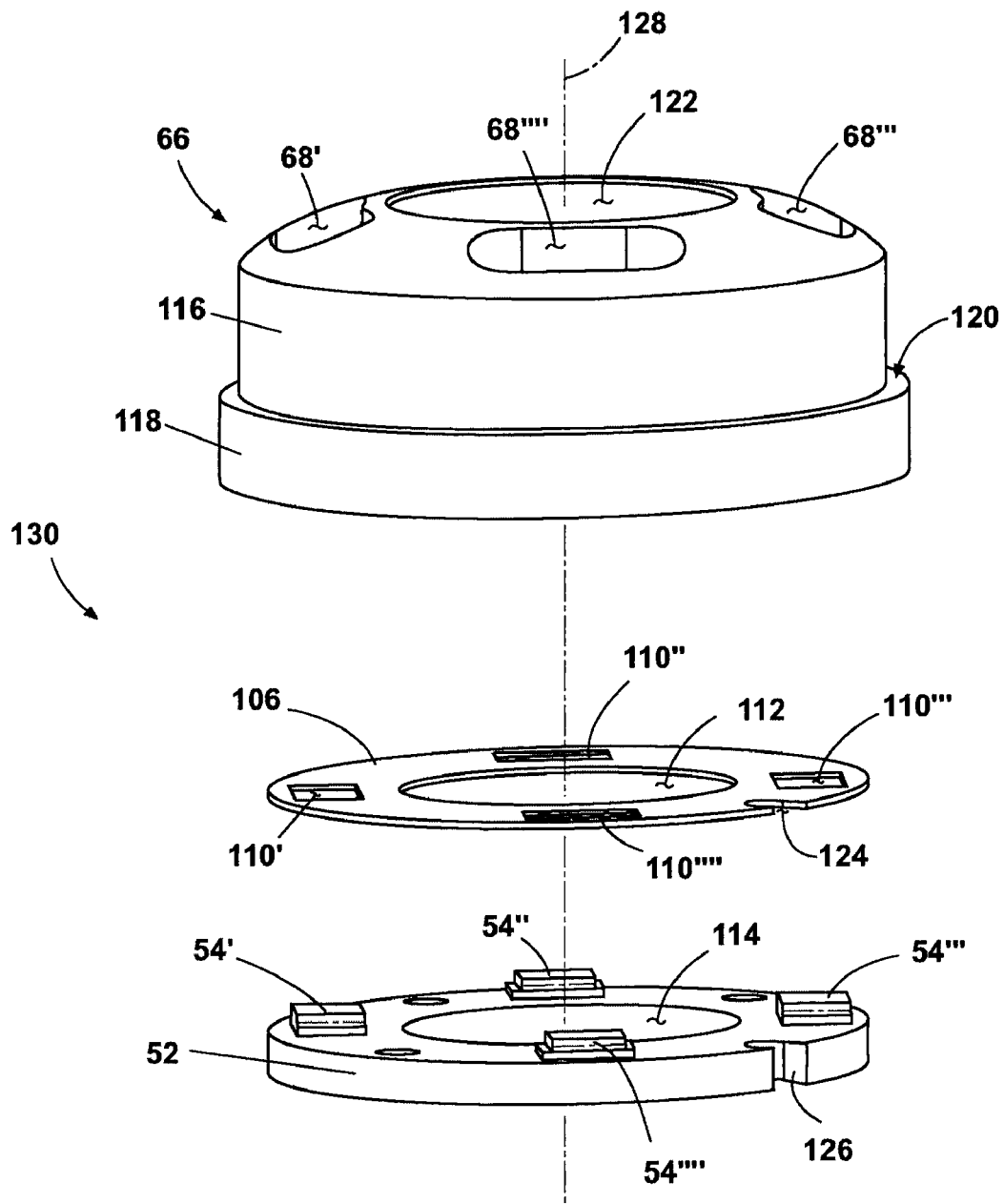
FIG. 13 is an assembly view of an imager cap, thermal gasket, and LED board sub-assembly.

Referring to FIG. 13, thermal gasket 106 is aligned with LEDs 54 of LED board 52 such that each of the semi-circular elongated apertures 110 defined for example as semi-circular elongated apertures 110', 110", 110''', 110'''' are coaxially aligned with each of LEDs 54', 54", 54''' and 54'''' respectively. Each of the semi-circular elongated apertures 110 and LEDs 54 are also coaxially aligned with individual ones of the light passages 68', 68" (not visible in this view), 68''', and 68'''' respectively. The first and second imaging lens receiving apertures 112, 114 are also coaxially aligned with a light/image receiving aperture 122 of imager cap 166. Imager cap 166 further includes a first cylinder portion 116 having a diameter smaller than a diameter of a second cylinder portion 118, thereby creating a seal member contact surface 120. Seal member contact surface 120 can be further used to provide additional hermetic sealing between imager cap 66 and imager nut 46 (not shown in this view). Thermal gasket 106 can further include a wire clearance slot 124 which is coaxially alignable with a wire clearance slot 126 created in LED board 52. Each of the imager cap 66, thermal gasket 106, and LED board 52 are coaxially alignable along a longitudinal axis 128 which also defines a longitudinal axis of imager head assembly 104. Imager cap 66, thermal gasket 106 and LED board 52 together define a sub-assembly 130.

Figure 16:
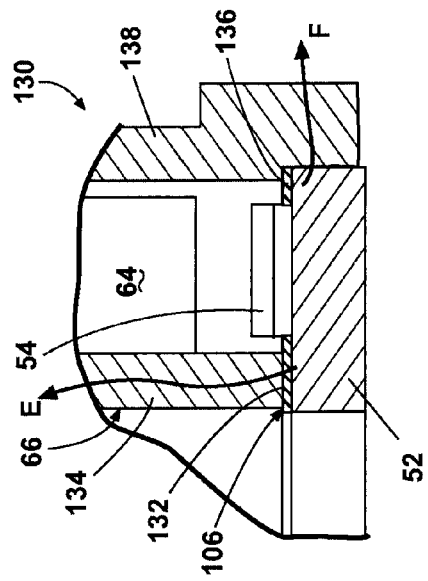
FIG. 16 is an exploded cross sectional side elevational view taken at area 16 of FIG. 15.
Figure 15:
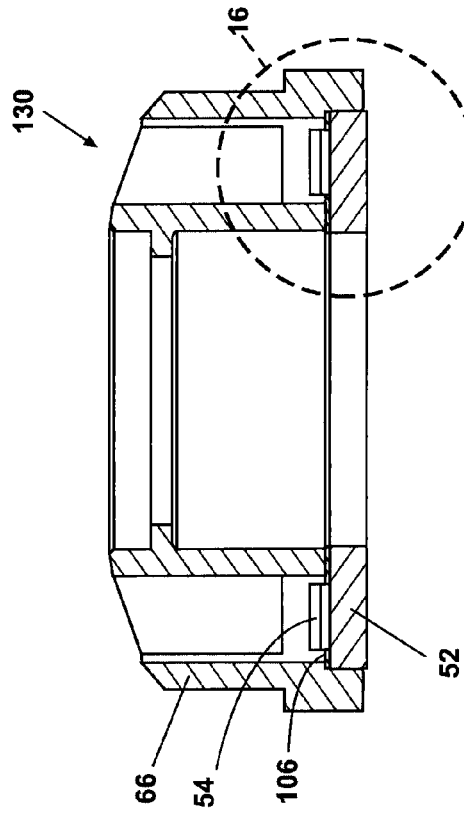
FIG. 15 is cross sectional side elevational view taken at section 15 of FIG. 14.
Figure 14:
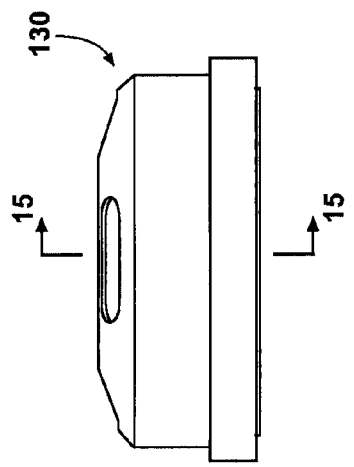
FIG. 14 is a front elevational view of the sub-assembly of FIG. 13.

Referring to FIGS. 14 through 16, sub-assembly 130 also provides physical contact between LED board 52 and thermal gasket 106 between a first thermal gasket portion 132 and an imager cap outer wall portion 134. In addition, sub-assembly 130 provides physical contact between LED board 52 and thermal gasket 106 between a second thermal gasket portion 136 of thermal gasket 106 and an imager cap inner wall portion 138. These contact regions create each of a fifth and a sixth heat transmission path "E", "F" for sub-assembly 130.

Figure 17:
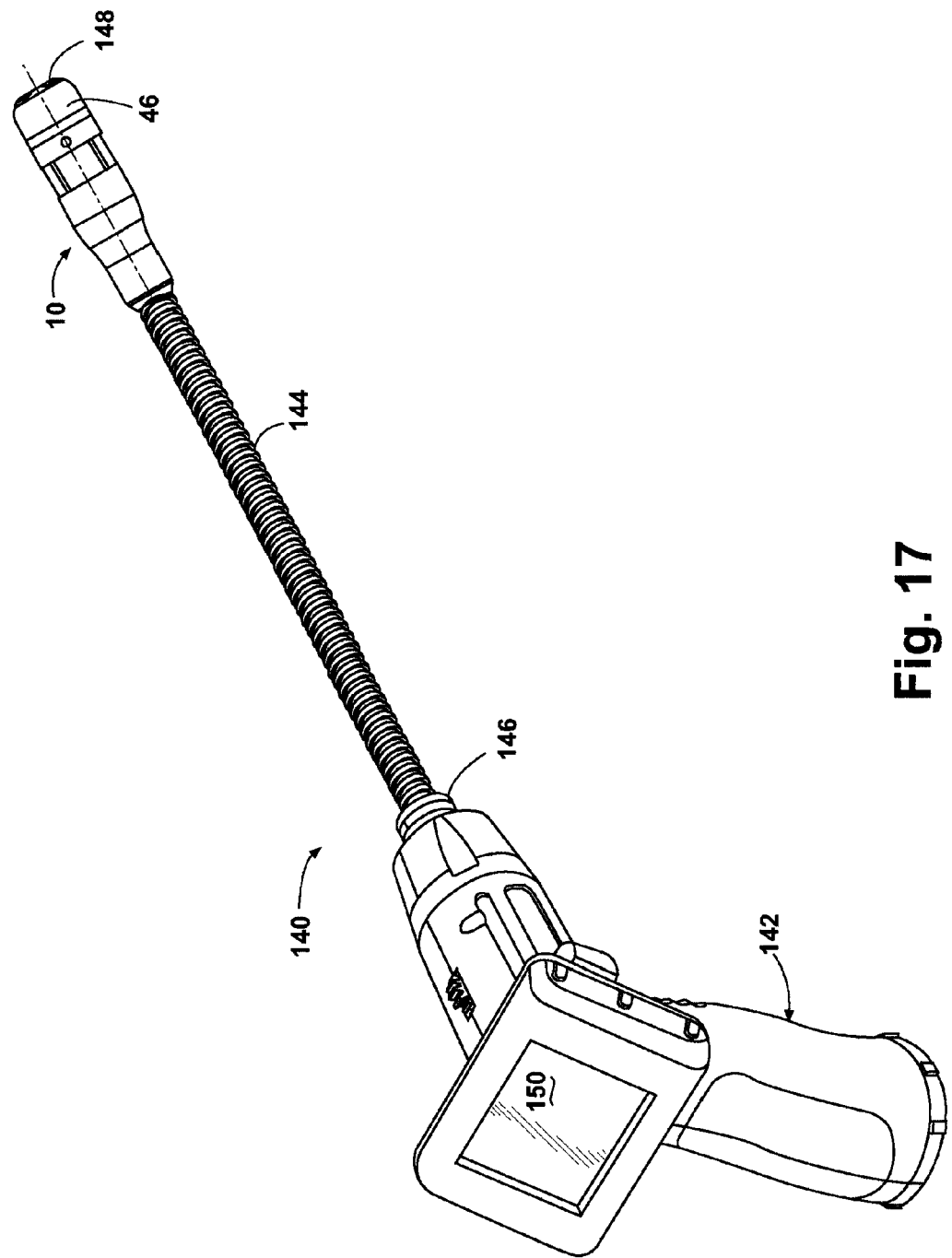
FIG. 17 is a perspective view of a remote inspection device having an imager head assembly of the present disclosure.

Referring to FIG. 17, an exemplary remote inspection device 140 having an imager head assembly 10 of the present disclosure includes a display housing 142. Display housing 142 can be a hand-held unit, having imager head assembly 10 connected to remote inspection device 140 using a flexible tube 144. Flexible tube 144 allows imager head assembly 10 to be remotely and movably displaced with respect to display housing 142. A housing connection sub-assembly 146 releasably connects flexible tube 144 to display housing 142. Imager head assembly 10 provides an image receiving end 148 adapted to receive and digitally send a viewed image from imager head assembly 10 to an image view screen 150 provided with display housing 142. The image view screen 150 is adapted present the digital signal image transferred by imager head assembly 10. Imager nut 46 is provided to releasably engage the image receiving end 148 of imager head assembly 10.

Referring again to FIGS. 1, 10, and 17, high intensity light emitting diodes used for LEDs 54 produce light from electrical power provided to LED board 52. LEDs 54 illuminate through light pipe unit 60 an area in a viewing range of imaging lens 40 of either imager assembly 10 or imager head assembly 104. The reflected light/image received through light receiving window 70 is converted via imager device 72 to a digital signal and transferred via a wiring harness (not shown) to the image view screen 150 of display housing 142.

The thermal dissipation provided by imager head assemblies of remote inspection devices of the present disclosure provide several advantages. By coupling the heat generating components, the LEDs 54, using light transmissive thermal adhesives, thermal grease material, and/or thermal gasket material to heat sink components of the imager head assemblies, improved conductive transfer is provided. A light transmissive, thermally conductive adhesive positioned between the LEDs and a light pipe unit precludes electrical conductance while improving heat transfer. The heat generated by high power LEDs can be dissipated in a compact imager head assembly to ambient to reduce thermal loading of the imager head assemblies and therefore life cycle improvements can be realized for digital signal imager head assemblies. High power as defined herein refers to power consumption greater than approximately 20 mW per LED.

What is claimed is:

1. An imager head assembly for a remote inspection device, comprising:
    an imager body;
    an imager nut coupled to the imager body;
    an imager cap positioned within and in direct contact with the imager nut;
    a circuit board having an outer perimeter surface slidably received within and in direct contact with an inner perimeter surface of the imager cap, the circuit board having at least one light emitting diode (LED) fixedly connected thereto;
    a light pipe unit slidably received in the imager cap and connected to the circuit board, the light pipe unit having at least one light pipe contacting the imager cap and coaxially positioned with respect to the at least one LED; and
    a light transmissive, thermally conductive adhesive applied over all of a face of the light pipe unit, the circuit board including the at least one LED, and the outer perimeter surface of the circuit board, the adhesive fixedly retaining the circuit board to the imager nut, and fixedly retaining the light pipe unit to the imager cap, the adhesive creating a first heat transmission path conductively dissipating heat generated by the at least one LED by contact between circuit board, the imager cap, and the imager nut, and a second heat transmission path conductively dissipating heat generated by the at least one LED via the light pipe unit to the imager cap.

2. The imager head assembly for a remote inspection device of claim 1, wherein:
    the imager body includes external threads; and
    the imager nut includes internal threads threadably engaged with the external threads of the imager body to couple the imager nut in contact with the imager cap to the imager body.

3. The imager head assembly for a remote inspection device of claim 1, wherein:

the at least one LED includes four equidistantly spaced high power LEDs operating to generate light to illuminate an object located proximate to the imager head assembly; and the at least one light pipe includes four light pipes individually coaxially positioned with respect to individual ones of the four LEDs.

4. The imager head assembly for a remote inspection device of claim 1, wherein the imager body, the imager cap, and the imager nut are each constructed of a thermally conductive metal material.

5. The imager head assembly for a remote inspection device of claim 1, further including a seal member positioned within an internal diameter of the imager nut and positioned directly between and in direct contact with both the imager cap and the imager body, the seal member compressed when the imager nut is coupled to the imager body to create a moisture and air seal between the imager nut and the imager body.

6. The imager head assembly of claim 1, further including a thermally conductive flexible gasket having a gap filling property, the gasket compressed between the circuit board and the light pipe unit when the imager nut is coupled to the imager body.

7. The imager head assembly of claim 6, wherein the flexible gasket includes an aperture coaxially aligned with the light pipe to promote light transmission from the LED through the light pipe unit.

8. The imager head assembly of claim 1, further comprising:
a lens mount positioned within and in contact with the imager housing, the lens mount having multiple alignment pins; and
a thermal grease coated on individual surfaces of the lens mount to promote thermal conductivity between the circuit board, the lens mount, and the imager housing.

9. The imager head assembly of claim 8, wherein the alignment pins are created on and extend from the lens mount, the alignment pins individually insertable into individual alignment pin apertures of the second circuit board to non-rotatably fix the second circuit board with respect to the lens mount.

10. An imager head assembly for a remote inspection device, comprising:
an imager nut threadably connected to an imager body;
an imager cap positioned within and in direct contact with the imager nut;
a first circuit board positioned within the imager cap, the first circuit board having four equidistantly spaced high power light emitting diodes (LEDs) connected thereto operating to generate light to illuminate an object located proximate to the imager head assembly, and having an outer perimeter surface received within and in direct contact with an inner perimeter surface of the imager cap;
a lens mount positioned in the imager body having multiple integrally extending alignment pins of the lens mount received in the first circuit board to non-rotatably mount the first circuit board to the lens mount;
a second circuit board positioned within the imager body receiving second alignment pins of the lens mount to non-rotatably mount the second circuit board to the lens mount, the second circuit board having an imager device connected to the second circuit board, the imager device adapted to receive the light emitted by the LEDs and reflected off the object and to transmit a digital signal representing an image of the object; and
a light transmissive, thermally conductive adhesive applied over all of the first circuit board including the LEDs, an outer perimeter surface of the first circuit board, and the lens mount, the adhesive fixedly connecting the first circuit board to the imager nut and the lens mount to the imager body, the adhesive creating a first heat transmission path conductively dissipating heat generated by the LEDs by contact between the first circuit board, the imager cap, and the imager nut, and a second heat transmission path conductively dissipating heat generated by the LEDs via the first circuit board, the lens mount, and the imager body.

11. The imager head assembly of claim 10, further including a light transmissive light pipe unit positioned proximate the first circuit board, the light pipe unit constructed of a transparent polymeric material integrally forming both a base ring and a plurality of light pipes which transversely extend from the base ring, the light pipe unit having individual ones of the light pipes individually aligned with each of the LEDs to permit light emitted by the LEDs to pass through the light pipe unit and out of the imager head assembly.

12. The imager head assembly of claim 11, where the imager cap is adapted to slidably receive both the light pipe unit and the first circuit board, the imager cap being constructed of a thermally conductive metal material.

13. The imager head assembly of claim 10, further including:
a light pipe unit slidably received in the imager cap and contacting the first circuit board, the light pipe unit having four light pipes each contacting the imager cap and coaxially positioned with respect to one of the LEDs; and
wherein the light transmissive, thermally conductive adhesive is also applied over all of a face of the light pipe unit to fixedly connect the light pipe unit to the imager cap.

* * * * *